(12) United States Patent
Davis et al.

(10) Patent No.: US 7,927,588 B2
(45) Date of Patent: Apr. 19, 2011

(54) SKIN DRESSINGS CONTAINING OXIDOREDUCTASE ENZYME

(75) Inventors: Paul James Davis, Bedford (GB); Andrew John Austin, Northants (GB)

(73) Assignee: Archimed LLP, Bedford (GB)

( * ) Notice: Subject to any disclaimer, the term of this patent is extended or adjusted under 35 U.S.C. 154(b) by 514 days.

(21) Appl. No.: 10/557,998

(22) PCT Filed: Jun. 4, 2004

(86) PCT No.: PCT/GB2004/002374
§ 371 (c)(1),
(2), (4) Date: Nov. 22, 2005

(87) PCT Pub. No.: WO2004/108176
PCT Pub. Date: Dec. 16, 2004

(65) Prior Publication Data
US 2006/0275350 A1    Dec. 7, 2006

(30) Foreign Application Priority Data
Jun. 9, 2003 (GB) .................................. 0313217.2

(51) Int. Cl.
*A61K 38/44* (2006.01)
(52) U.S. Cl. .......... 424/94.4; 435/25; 435/176; 435/177; 435/182; 435/189; 435/190
(58) Field of Classification Search ............ 435/25, 435/176, 177, 182, 189, 190; 424/94.4
See application file for complete search history.

(56) References Cited

U.S. PATENT DOCUMENTS

| | | |
|---|---|---|
| 3,546,070 A | 12/1970 | Yoshinaga |
| 4,010,259 A | 3/1977 | Johansson |
| 4,278,548 A | 7/1981 | Bettinger et al. |
| 4,312,833 A | 1/1982 | Clough et al. |
| 4,327,731 A * | 5/1982 | Powell .......................... 604/361 |
| 4,391,799 A | 7/1983 | Mason et al. |
| 4,452,892 A | 6/1984 | Rosevear |
| 4,476,108 A | 10/1984 | Kessler et al. |
| 4,576,817 A | 3/1986 | Montgomery |
| 4,581,336 A * | 4/1986 | Malloy et al. ................. 435/176 |
| 4,657,864 A | 4/1987 | Lo |
| 4,665,028 A * | 5/1987 | Amotz .......................... 435/174 |
| 4,746,514 A | 5/1988 | Warne |
| 4,775,626 A | 10/1988 | Armenta et al. |
| 4,783,448 A | 11/1988 | Johansson |
| 5,196,190 A | 3/1993 | Nangia et al. |
| 5,232,914 A | 8/1993 | Fellman |
| 5,372,802 A | 12/1994 | Barrows et al. |
| 5,399,353 A | 3/1995 | Bartnik et al. |
| 5,455,042 A | 10/1995 | Sakai et al. |
| 5,483,697 A * | 1/1996 | Fuchs ............................ 2/161.7 |
| 5,552,316 A | 9/1996 | Savage |
| 5,607,681 A | 3/1997 | Galley et al. |
| 5,648,075 A | 7/1997 | Kessler et al. |
| 5,652,274 A | 7/1997 | Martin |
| 5,696,456 A | 12/1997 | Lee |
| 5,762,638 A | 6/1998 | Shikani et al. |
| 5,792,090 A | 8/1998 | Ladin |
| 5,804,213 A | 9/1998 | Rolf |
| 5,849,241 A | 12/1998 | Connan |
| 6,103,275 A | 8/2000 | Seitz et al. |
| 2001/0041188 A1 | 11/2001 | Gibbins et al. |
| 2002/0006634 A1 | 1/2002 | Han et al. |
| 2002/0037270 A1 * | 3/2002 | Munro et al. .............. 424/78.17 |
| 2003/0082225 A1 | 5/2003 | Mason |
| 2003/0225356 A1 | 12/2003 | Kulichikhin et al. |
| 2005/0181026 A1 | 8/2005 | Davis et al. |
| 2006/0034816 A1 | 2/2006 | Davis et al. |
| 2006/0281165 A1 | 12/2006 | Davis et al. |
| 2007/0148117 A1 | 6/2007 | Davis et al. |

(Continued)

FOREIGN PATENT DOCUMENTS
DE          40 26 153          2/1992
(Continued)

OTHER PUBLICATIONS

Carlsson "Bactericidal effect of hydrogen peroxide is prevented by the lactoperoxidase-thiocyanate system under anaerobic conditions" Infection and Immunity 1190-1192 (1980). Graf et al., "Method for determination of hydrogen peroxide, with its application illustrated by glucose assay" Clin. Chem., 26(5):658-660 (1980).
Kompendium Pharma. '98 (handbook for the pharmaceutical preparation of non-standard pharmacy products) with translation of p. 224.
Sohail et al. "Divalent Cation Induced Changes in Structural Properties of the Dimeric Enzyme Glucose Oxidase: Dual Effect of Dimer Stabilization and Dissociation with Loss of Cooperative Interactions in Enzyme Monomer" Biochemistry 41(22):7142-7149 (2002).

*Primary Examiner* — Allison M. Ford
*Assistant Examiner* — Susan E. Fernandez
(74) *Attorney, Agent, or Firm* — Morgan, Lewis & Bockius LLP

(57) ABSTRACT

A skin dressing comprises a first dressing component (16) carrying oxidoreductase enzyme in dried condition; and a second dressing component (18) carrying a source of water, such that when the first and second dressing components are placed in fluid communication with each other, water migrates from the second component towards the first comportent and acts to hydrate enzyme carried by the first component, at least at the surface of the first component. The dressing components are kept separate before use, e.g. being sealed in separate sterile, water-impervious packages such as laminated aluminum foil pouches. In use of the dressing, the second dressing component is located on the skin of a human or animal, e.g. over a wound to be treated or on a region of skin to be treated for cosmetic or therapeutic purposes such as for treatment of acne or other skin conditions. The first dressing component is placed on top of the second component in fluid communication therewith. In embodiments comprising only first and second dressing components, the first dressing component is placed in direct contact with the second dressing component. Water from the second component migrates towards the first comportent and acts to hydrate enzyme carried by the first component, at least at points of contact at the interface between the first and second components. Once hydrated, the oxidoreductase enzyme can immediately begin functioning in known manner with beneficial effects.

27 Claims, 2 Drawing Sheets

U.S. PATENT DOCUMENTS

Figure 1:
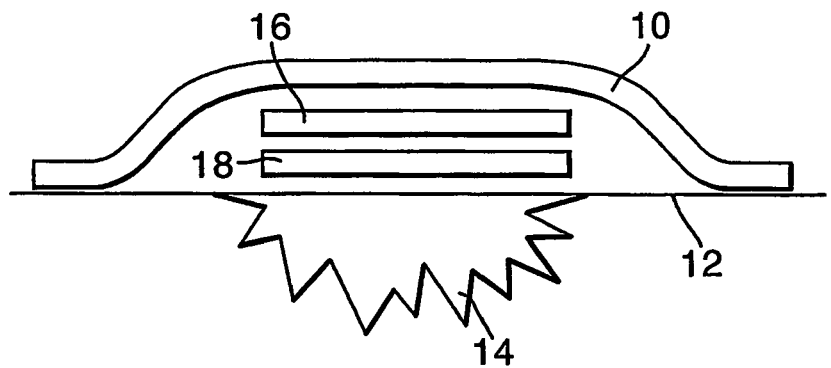

| | | |
|---|---|---|
| 2007/0190122 A1 | 8/2007 | Davis et al. |
| 2009/0081279 A1 | 3/2009 | Jezek et al. |
| 2009/0169600 A1 | 7/2009 | Davis et al. |

FOREIGN PATENT DOCUMENTS

| | | |
|---|---|---|
| EP | 0307376 | 3/1989 |
| EP | 1429617 | 6/2004 |
| GB | 2024012 | 1/1980 |
| WO | WO 91/11105 | 8/1991 |
| WO | WO 94/04127 | 3/1994 |
| WO | WO 97/02811 | 1/1997 |
| WO | WO 98/20015 | 5/1998 |
| WO | WO 98/22513 | 5/1998 |
| WO | WO 99/12581 | 3/1999 |
| WO | WO 99/65538 | 12/1999 |
| WO | WO 0128600 | 4/2001 |
| WO | WO 01/96422 | 12/2001 |
| WO | WO 01/98286 | 12/2001 |
| WO | WO 03/017989 | 3/2003 |
| WO | WO 03/090800 | 11/2003 |
| WO | WO 2004/091675 | 10/2004 |
| WO | WO 2004/093786 | 11/2004 |
| WO | WO 2004/108176 | 12/2004 |
| WO | WO 2004/108917 | 12/2004 |
| WO | WO 2004/112851 | 12/2004 |
| WO | WO 2005/072783 | 8/2005 |
| WO | WO 2005/072784 | 8/2005 |
| WO | WO 2006/062679 | 6/2006 |
| WO | WO 2006/095193 | 9/2006 |
| WO | WO 2007/134304 | 11/2007 |
| WO | WO 2008/009925 | 1/2008 |

* cited by examiner

SKIN DRESSINGS CONTAINING OXIDOREDUCTASE ENZYME

FIELD OF THE INVENTION

This invention relates to skin dressings for application to a part of a human or animal body for treatment of skin, and relates particularly (but not exclusively) to wound dressings for treatment of compromised skin, particularly skin lesions, i.e. any interruption in the surface of the skin, whether caused by injury or disease, including skin ulcers, burns, cuts, punctures, lacerations, blunt traumas, acne lesions, boils etc.

BACKGROUND TO THE INVENTION

Skin and wound dressings are designed to undertake a number of important functions to aid the process of healing. Experts agree on most of the functions that an ideal dressing should provide, and these include:
  Donation of moisture to dry wounds
  Absorption of excess fluid from weeping wounds
  Maintenance of a moist environment around the wound bed
  Binding of water sufficiently well to prevent maceration (water-logging) of the normal tissue
  Aiding debridement (removal of dead tissue and scar material)
  Prevention of infection and provision of a barrier to escaping or invading microbes
  Killing infecting microbes
  Cushioning against further physical trauma
  Maintaining an optimum temperature through thermal insulation
  Allowing ingress of plentiful oxygen
  Soothing painful and inflamed open wound sites
  Flexibly adapting to the shape of the wound site
  Keeping its physical integrity so that fragmented dressing debris is not left in the wound
  Exerting no cytotoxic nor physically damaging effects on the healing cells.

In addition, the handling and physical design characteristics should make the dressing easy to use and comfortable to wear. For storage and distribution purposes, the dressing should be stable at ambient temperatures, and robust. Ideally it should be simple to manufacture, in order to allow its production and sale at a price that is affordable for widespread use.

These and other demands make the design of an ideal wound dressing almost impossible. To date, all wound dressings are a compromise, such that none offers all of the much desired characteristics in one product. For this reason, there are numerous different wound dressings on the market, and the typical nurse caring for patients with wounds needing professional care will select different dressings for different wounds and for wounds at different phases of the wound healing process. Manufacturers are constantly seeking new ways to make more effective wound dressings, which means that they are trying to make dressings that incorporate more of the characteristics and functions listed above. With the achievement of each new benefit, the cause of improved patient welfare is advanced, as the result of faster healing, reduction of pain and improvement in the quality of life. Medical care in general can benefit from such progress. Although these advanced, "active" dressings usually cost more, they can reduce the overall time during which a wound needs attention and reduce the amount of nursing time devoted to frequent changes of dressing. This drives down the huge cost borne by modern society in caring for wounds.

The invention described here is concerned with improving the performance of wound dressings, in terms of the features listed above.

When considering this list of requirements, it soon becomes clear that many of the demands seem to be contradictory. For example, a dressing that donates moisture would not, at first sight, be expected to be able to absorb water—the two functions seem to be in opposition to each other. Another example is the need simultaneously to provide a cushioning effect and an efficient inflow of oxygen, whilst preventing dryness. It would be expected that a dressing bulky enough to act as a cushion or shock absorber would inevitably provide a barrier to oxygen ingress, especially if the whole of the surface is sealed to keep moisture in. For this reason, some wound dressings are compound structures, made up from different layers, each with a different function and role. In fact, practitioners often mix and match different dressings from different manufacturers to produce their own compound structures, with highly variable results. Compound dressings need to be designed to work as an integrated whole, or the components may interact with each other to inhibit or neutralise the effects designed to operate on the wound.

Wounds frequently become infected. Wound dressings may carry antiseptic substances, and the physical protection they provide prevents ingress of extra infecting microbes, although this microbial exclusion is seldom absolute. Antiseptic substances carried on the dressing pad are not usually very effective, possibly because they do not readily diffuse into the wound at a steady rate. Moreover, the most effective substances, antibiotics, are not available for routine use, because of the ever-present problems of emerging drug resistance.

Hydrogen peroxide ($H_2O_2$) is a known antimicrobial substance with many advantages. It is produced naturally in the body by white blood cells as part of the immune defense activities in response to infection. There are no known microbial evasion mechanisms by which microbes can escape its effects and it has a short lifetime, very rapidly breaking down to water and oxygen in the tissues. It therefore does not accumulate to dangerous levels. When it is to be applied topically (e.g. to treat acne), its effectiveness is enhanced by the fact that it readily penetrates the skin surface to reach underlying sites of infection.

As hydrogen peroxide is so beneficial, it has been used for many years as an anti-microbial substance for cleansing wounds of all kinds and as a biologically compatible general antiseptic. In particular, hydrogen peroxide-containing ointments have been used, e.g., for treatment of leg ulcers, pressure sores, minor wounds and infection. There are, however, problems associated with the use of hydrogen peroxide. Hydrogen peroxide solution is very unstable and is readily oxidised to water and oxygen; further, hydrogen peroxide at high concentration can be damaging to normal skin and to cells responsible for healing in the wound bed. It is very difficult or even impossible to use hydrogen peroxide as part of a pre-dosed wound dressing: its instability would make for a product with a relatively short shelf-life, and dosing at the point of application would still not provide a sustained delivery over a usefully prolonged period. When it is used in wound treatment (as described in the British Pharmacopoeia, for example) high concentrations (typically 3%) are needed to achieve a powerful antimicrobial effect over a very short time interval. Even this type of short burst can be effective, because of the great effectiveness of hydrogen peroxide, but there is the further disadvantage that such high concentrations can be relatively damaging to host cells and can impede the healing process. For this reason, use of hydrogen peroxide tends to be restricted to initial clean-up and sterilisation of wounds. Even so, it is a natural defense substance, produced by the body's own cells (at lower concentrations) and it is increasingly recognised as an intercellular and intracellular messenger molecule, involved in cell to cell molecular signalling and regulation. Undoubtedly, hydrogen peroxide is potentially a very beneficial multifaceted healing agent, if it can be used at the right concentrations and in the appropriate time course.

U.S. Pat. No. 4,576,817 proposes a bacteriostatic fibrous wound dressing incorporating dry enzymes such as glucose oxidase and lactoperoxidase to generate e.g. hydrogen peroxide and hypoiodite on contact with serum.

WO 01/28600 discloses a wound dressing including dry glucose oxidase, dry lactoperoxidase and an iodide salt in a polymeric matrix. The glucose oxidase catalyses an oxidation reaction of glucose present in body fluids of a wound site to generate hydrogen peroxide. The action of lactoperoxidase on hydrogen peroxide and iodide generates elemental iodine, which is a powerful anti-infective agent.

The wound dressings disclosed in U.S. Pat. No. 4,576,817 and WO 01/28600 rely on use of water in body fluids for hydrating dried enzyme. This inevitably leads to a delay between application of such a dressing to a wound and functioning of enzyme-based reactions.

SUMMARY OF THE INVENTION

According to the present invention there is provided a skin dressing, comprising a first dressing component carrying oxidoreductase enzyme in dried condition; and a second dressing component carrying a source of water, such that when the first and second dressing components are placed in fluid communication with each other, water migrates from the second component towards the first component and acts to hydrate enzyme carried by the first component, at least at the surface of the first component.

The dressing components are kept separate before use, e.g. by being sealed in separate sterile, water-impervious packages such as laminated aluminum foil pouches.

In use of the dressing, the second dressing component is located on the skin of a human or animal, e.g. over a wound to be treated or on a region of skin to be treated for cosmetic or therapeutic purposes such as for treatment of acne or other skin conditions. The first dressing component is placed on top of the second component in fluid communication therewith. In embodiments comprising only first and second dressing components, the first dressing component is placed in direct contact with the second dressing component. Water from the second component migrates towards the first component and acts to hydrate enzyme carried by the first component, at least at points of contact at the interface between the first and second components. Once hydrated, the oxidoreductase enzyme can immediately begin functioning, in known manner, with consequent beneficial effects, e.g. as disclosed in U.S. Pat. No. 4,576,817.

The dressing components are used in such a way that the first component does not contact the skin and all water for enzyme hydration comes from the second component. A dressing in accordance with the invention is self-contained and does not rely on water in body fluids for enzyme hydration, e.g. as in the dressings of U.S. Pat. No. 4,576,817 and WO 01/28600, but instead includes the necessary water in the second component. This arrangement thus provides for controlled, predictable enzyme hydration. Further, because the enzyme does not contact the skin there is less scope for enzyme degradation by proteases present in a wound.

The invention is based on the surprising discovery that dried enzyme in the first component can be effectively hydrated relatively rapidly, at least at the surface thereof, with water from the second component, even in circumstances where it would not be expected that water would migrate from the second component towards the first component.

In use of the dressing, the oxidoreductase enzyme catalyses a reaction of an appropriate substrate with oxygen to produce hydrogen peroxide. The substrate may either be naturally present in body fluids and/or be supplied separately and/or be incorporated into the dressing. Oxidoreductase enzymes suitable for use in the invention and the corresponding substrates (which are present in blood and tissue fluids) include the following:

| Enzyme | Substrate |
| --- | --- |
| Glucose oxidase | β-D glucose |
| Hexose oxidase | Hexose |
| Cholesterol oxidase | Cholesterol |
| Galactose oxidase | D-galactose |
| Pyranose oxidase | Pyranose |
| Choline oxidase | Choline |
| Pyruvate oxidase | Pyruvate |
| Glycollate oxidase | Glycollate |
| Aminoacid oxidase | Aminoacid |

The currently preferred oxidoreductase enzyme is glucose oxidase. This catalyses reaction of β-D-glucose substrate to give hydrogen peroxide and gluconic acid.

A mixture of oxidoreductase enzymes may be used.

If the reaction occurs on or in the vicinity of the skin, the hydrogen peroxide so produced can have a localised antibacterial effect.

Alternatively or additionally, the hydrogen peroxide generated in this way may be used in a two stage arrangement, with the hydrogen peroxide undergoing a reaction catalysed by a peroxidase enzyme to produce a variety of species including reactive oxygen intermediates that have antimicrobial properties and that can therefore assist in promoting wound healing. For such embodiments, the dressing includes a peroxidase enzyme, preferably present in hydrated condition. As a further possibility the hydrogen peroxide can react directly in a non-catalysed manner with substances such as iodide ions to generate molecular iodine.

Peroxidase enzymes useful in the invention include lactoperoxidase, horseradish peroxidase, iodide peroxidase, chloride peroxidase and myeloperoxidase, with lactoperoxidase currently being favoured.

A mixture of peroxidase enzymes may be used.

The active species produced by the action of peroxidases are difficult to define or characterise, and will to some extent depend on the particular peroxidase in question. For example, some reactions catalysed by horseradish peroxidase are different to the reactions catalysed by lactoperoxidase. The detailed chemistry is complicated by the fact that the products are so reactive that they rapidly give rise to other, associated products that are also very reactive. It is believed that the reactions are similar to those of the "oxidative burst" reactions identified in neutrophil and macrophage leukocytes of the human body.

The dressing desirably includes a source of substrate for the oxidoreductase enzyme, e.g. glucose for glucose oxidase. Preferably the glucose is in the form of pure, pharmaceutical grade material. Glucose can also be supplied in the form of honey which provides naturally other benefits such as healing and antimicrobial factors. The substrate is preferably incorporated in the second dressing component. Alternatively, the substrate may be present in a separate third dressing component that is preferably located in use between the first and second dressing components. In this case, the first and second dressing components are not in direct contact but are nevertheless in fluid communication via the third component, with water migrating from the second component, through the third component to the first component.

It is helpful to balance the relative amounts of enzyme and substrate so as to produce an excess of hydrogen peroxide which can be used to deliver oxygen to the wound bed or underlying tissues via the effects of catalase and other hydrogen peroxide-decomposing substances naturally present. It is believed that oxygen delivered in this way can encourage the formation of new blood vessels in the recovering wound (angiogenesis, or neovascular growth), stimulate the proliferation of new tissue-forming cells and control enzymes (proteases) responsible for helping to reshape the developing new tissue.

The substrate, e.g. glucose, may be present in various forms including dissolved within a hydrated hydrogel structure, present as a slowly dissolving solid, or encapsulated within another structure for slow release.

By providing an excess of substrate, so the dressing is able to function in use to generate and hold antimicrobial species over an extended period of time, typically 1-2 days, where substrate-containing hydrated gel or gels are formulated to retard flow of substrate to the enzymes, e.g. by extensive hydrogen bonding to impede diffusion through the or from the hydrogel in which they were originally supplied.

The antimicrobial efficiency of the system can be further enhanced by the inclusion of iodide ions, which can be oxidised to elemental iodine (which is a known powerful antimicrobial agents, e.g. as discussed in WO 01/28600) by the action of hydrogen peroxide, with or without catalytic enhancement. Thus, the dressing desirably includes a supply of iodide ions, e.g. potassium iodide or sodium iodide. The supply of iodide ions may be present either in the second dressing component or in an additional membrane or gauze or other suitable layer. As iodine is also relatively toxic to host cells in the wound (e.g. epithelial cells, keratinocytes, white blood cells) it may not be advantageous to generate iodine continuously at a high concentration throughout the time that the formulation is in use in contact with the skin. Thus, in a preferred embodiment, the supply of iodide ions, e.g. iodide salt, is provided in a relatively quick-release form. In this way, the hydrogen peroxide produced initially, in a first phase of activity, is substantially consumed in an iodine-generating reaction, exposing the skin (e.g. wound) to a surge of iodine, the duration of which can be controlled by the amount, release-rate and position of the iodide supply. Such an iodine surge can be very useful in quickly ridding a wound of a microbial burden, and its relatively short duration allows healing by minimising damage to growing cells and their repairing activity. Once the iodide has been consumed, the system automatically reverts, in a subsequent phase of activity, to the production of hydrogen peroxide and oxygen released therefrom, which maintains sterility and kills anaerobic bacteria under the dressing, e.g. at the wound surface. In other embodiments, however, it may be desired for the source of iodide ions to be such as to provide, in use, a sustained flux of iodine for release into a wound, in addition (and in proportion) to hydrogen peroxide. The supply of iodide may alternatively be located with the source of substrate for the oxidoreductase enzyme, as discussed above, e.g. in a hydrated gel. The iodide may be present in various forms, including dissolved within a hydrated gel structure, present as a slowly dissolving solid, or encapsulated within another structure for slow release. Iodide salt may be present, e.g. in an amount up to about 2% by weight.

The dressing components (first component, second component and third component if present) are desirably in the form of layers, such as sheets or slabs, of material, that can be placed on top of each other to produce a dressing of layered construction.

The first component comprises a support or carrier, preferably in the form of a layer of material, carrying enzyme. In a simple case, the support or carrier comprises a layer of material such as a cotton pad (e.g. as disclosed in U.S. Pat. No. 4,576,817), a sheet of cotton gauze, or a sheet of absorbent paper such as blotting paper, with dried enzyme. Using such carrier materials, water migration from the second component is sufficient to hydrate and activate enzyme, at least at or near the surface of the carrier, sufficiently rapidly to give useful results. With such supports it is surprisingly found that water migration is such that there is sufficient moisture present at the surface of the first component in contact or fluid communication with the second component so that at least the enzyme carried on or very near that surface becomes active, even if there is not sufficient movement of water into the dried enzyme layer to hydrate the whole of the first component. Activation of surface enzyme only is nevertheless sufficient to give useful results. It is, however, preferred to use a support or carrier material designed for enhanced and rapid rehydration of enzyme. For example, good results have been obtained with use of dried hydrogels as the first component carrier material.

Hydrogel material including the enzyme is typically cast to form a slab, and then dried to form the first dressing component.

The hydrogel conveniently comprises hydrophilic polymer material. Suitable hydrophilic polymer materials include polyacrylates and methacrylates, e.g. as supplied by First Water Ltd in the form of proprietary hydrogels, including poly(-2-acrylamido-2-methylpropane sulphonic acid) (poly-AMPS) or salts thereof (e.g. as described in WO 01/96422), polysaccharides e.g. polysaccharide gums particularly xanthan gum (e.g. available under the Trade Mark Keltrol), various sugars, polycarboxylic acids (e.g. available under the Trade Mark Gantrez AN-169 BP from ISP Europe), poly (methyl vinyl ether co-maleic anhydride) (e.g. available under the Trade Mark Gantrez AN 139, having a molecular weight in the range 20,000 to 40,000), polyvinyl pyrrolidone (e.g. in the form of commercially available grades known as PVP K-30 and PVP K-90), polyethylene oxide (e.g. available under the Trade Mark Polyox WSR-301), polyvinyl alcohol (e.g. available under the Trade Mark Elvanol), cross-linked polyacrylic polymer (e.g. available under the Trade Mark Carbopol EZ-1), celluloses and modified celluloses including hydroxypropyl cellulose (e.g. available under the Trade Mark Klucel EEF), sodium carboxymethyl cellulose (e.g. available under the Trade Mark Cellulose Gum 7LF) and hydroxyethyl cellulose (e.g. available under the Trade Mark Natrosol 250 LR).

Mixtures of hydrophilic polymer materials may be used in a gel.

Poly-AMPS and salts thereof are the currently preferred materials.

The hydrophilic polymer material is desirably present at a concentration of at least 1%, preferably at least 2%, more preferably at least 5%, possibly at least 10%, by weight based on the total weight of the gel.

By using a gel comprising a relatively high concentration (say 10% by weight) of hydrophilic polymer material, the gel can function particularly effectively to take up water from the second dressing component in use of the dressing.

Good results have been obtained using a dried hydrogel comprising 10% by weight of poly-AMPS and/or a salt or salts thereof.

The gel may be cross-linked. For example, the gel may comprise an alginate gel, e.g. formed from alginic acid cross-linked in known manner, e.g. by use of calcium chloride. Cross-linked gels form an entrapping biopolymer matrix that can retain the enzyme within the gel if the degree of cross-linking is sufficiently tight, thus preventing release of the enzyme into the wound bed in use of the dressing. The gel may be in the form of beadlets, beads, slabs or extruded threads etc.

The hydrogel, particularly a cross-linked gel, may be cast around a mechanical reinforcing structure, such as a sheet of cotton gauze or an inert flexible mesh, e.g. to provide a structurally reinforced hydrogel layer or slab.

The enzyme or enzymes may be immobilised so they can be prevented from being released into a wound, where they would have the potential to trigger undesirable allergic responses (being generally derived from non-human sources, e.g. with most commercially available glucose oxidase being derived from the fungus *Aspergillius niger* and with lactoperoxidase typically being extracted from bovine milk) and would also be susceptible to degradation by the effect of proteases present in a wound.

An enzyme may be immobilised in known manner, e.g. by being irreversibly bound to a solid support such as a particle, bead or fibre, e.g. of cellulose, silica, polymer etc., using coupling methods known to those skilled in the art. Incorporating an enzyme in a cross-linked alginate gel as discussed above, e.g. in the form of beadlets, slabs or extruded threads, also has the effect of immobilising the enzymes. Known encapsulation techniques using polyamide are also appropriate.

The second dressing component comprises a support or carrier, preferably in the form of a layer of material, carrying water. In a simple case, the support or carrier may comprise a sheet or slab of water-absorbent material such as sponge material or agar. Such a support is not ideal as it is not well suited to absorb wound fluid. However, a dressing with such a second component support could nevertheless be beneficial for use with dry wounds, especially where the aim was rapid moisturisation and delivery of antimicrobial effects and/or oxygenation. It is, however, generally preferred to use a hydrated hydrogel as the second component (with the gel constituting the carrier or support). Suitable gel materials include those discussed above in connection with the first dressing component, (but in hydrated condition) with poly-AMPS and salts thereof being the currently preferred materials. Hydrated hydrogels have various benefits and advantages for this purpose, including the following:

- they form soft, flexible slabs that conform to the contours of skin surface with soothing and comfortable effects for a user
- they are able to bind large quantities of water tightly and are found to function in use as very effective absorbers of moisture, e.g. wound exudate, from the skin surface
- they can also act to moisturize dry skin surface or a dry wound by increasing the relative humidity of the skin micro-environment
- despite the tight binding of water, it is nevertheless surprisingly found that effective and rapid migration of water to the first component can occur.

Hydrated hydrogels thus have a combination of good dressing properties and good water donation properties and so are well suited to use as the second dressing component.

Good results have been obtained with a hydrated hydrogel comprising 20% by weight of poly-AMPS and/or a salt or salts thereof as the second component. Such a composition has optimised wound dressing properties, as discussed above, particularly exudate absorption properties and wound moisturizing properties.

The hydrated hydrogel desirably contains at least 30% by weight water, to provide an ample reservoir for hydration of enzyme of the first component. The gel may contain a significantly higher amount of water, e.g. up to about 98% by weight water in a simple alginate or agar gel. The current preferred 20% poly-AMPS gels referred to above contain about 60% by weight of water.

The first and second components are preferably selected to be matched to each other, to enhance and preferably optimise water migration from the second component to the first component, with the first component desirably having a higher affinity for water than the second component and so being able successfully to compete for water initially present in the second component. One convenient way of achieving this is for the components to include ingredients that are chemically identical or similar, or that are functionally similar in terms of hydration and water binding behaviour. For example, the first and second components may both include gel supports comprising the same polymers, e.g. poly-AMPS and/or a salt or salts thereof, with identical or different levels of cross-linker in the two gels (the gel of the first component being in dried condition while that of the second component is in hydrated condition). The first and second components may both include polymers that are functionally similar to each other in terms of hydration and water binding behaviour. For example, where the second component includes a support of poly-AMPS and/or a salt or salts thereof, the first component conveniently includes polyvinyl alcohol (PVA), which functions as a hydration enhancer in the first component. The first component may also include monomers that are identical or similar to monomers from which the polymeric support of the second component is formed. For example, where the second component includes a support of poly-AMPS and/or a salt or salts thereof, the first component conveniently includes AMPS and/or a salt or salt thereof.

The first dressing component desirably includes one or more hydration enhancers, present in a suitable amount to increase the affinity for water of the first component, thereby enhancing migration of water from the second component to the first component in use of the dressing. Useful hydration enhancers include dried sugars (especially sucrose and trehalose), glycerol and sorbitol. Inclusion in the first component of materials that are chemically identical or similar or that are functionally similar to materials in the second component, as discussed above, can also be considered as examples of hydration enhancers. Suitable amounts of hydration enhancers can be readily determined by experiment.

Particularly good results have been obtained with a dressing in which the first component comprises a support of dried hydrogel formed from 10% by weight poly-AMPS and/or a salt or salts thereof, carrying enzyme, and the second component comprises a support of hydrated hydrogel comprising 20% by weight of poly-AMPS and/or a salt or salts thereof. The second component contains at least 60% by weight of water. In such a dressing, the second component is optimised for skin-contact properties, including moisturizing and fluid-uptake properties, as discussed above, and the first component is optimised for its ability to extract water from the second component.

The first and/or second components conveniently include one or more moisturizer materials. Useful moisturizer materials include zinc lactate, glycerol and sorbitol. Suitable amounts of moisturizer materials can be readily determined by experiment.

As noted above, the substrate for the enzyme of the first component (e.g. glucose for glucose oxidase) is preferably present in the second dressing component. Where the substrate is present in a separate third component, the third component comprises a support or carrier, preferably in the form of a layer of material, carrying substrate. The support or carrier is conveniently a dried hydrogel polymer. Suitable polymer materials include those discussed above in connection with the first and second components. The third component, if present, is desirably matched to the first and second components to optimise water migration from the second component, through the third component to the first component.

The dressing conveniently includes, or is used with, a covering or outer layer for adhering the dressing to the skin of a human or animal subject (in known manner). At least part of the covering should be of oxygen-permeable material to enable oxygen from ambient air to pass through the covering and enter into the body of the dressing in use, where it is required as a cosubstrate of the oxidoreductase catalysed reaction. The oxygen-permeable material may be in the form of a "window" set into an otherwise relatively oxygen-impermeable covering, e.g. of possibly more robust material.

Optionally the covering includes a window (or further window) in or through which can be seen indicator means e.g. an indicator sheet or similar structure that indicates (e.g. by changing colour) when the dressing chemistry is active. A further indicator may optionally be provided, which indicates (e.g. by changing colour) when the dressing chemistry has expired.

A further useful option is to provide immobilised catalase enzyme on the inner surface of the covering (e.g. secured to adhesive thereof). This will function rapidly to break down any excess hydrogen peroxide which may escape from a wound area. This feature will prevent potentially damaging build-up of hydrogen peroxide in areas of normal, undamaged skin.

It has been found that dressings in accordance with the invention act as efficient transporters of oxygen from the ambient atmosphere to a wound site, which has benefits for wound healing. In particular, the rate of oxygen transported through a dressing in accordance with the invention is greater than that of a similar dressing without oxidoreductase enzyme. The reason for this, and resulting benefits, are described below.

When a conventional dressing is applied to the surface of a wound, the supply of oxygen from the atmosphere is generally inhibited and the wound becomes relatively deprived of oxygen (hypoxic or even anoxic). Hypoxia or, worse, anoxia are frequently encountered conditions known to be detrimental to wound healing, because the cells responsible for the healing (keratinocytes and epithelial cells) and the leukocytes that fight infection and control the process, all need oxygen if they are to thrive. Phagocytic leukocytes need plentiful oxygen if they are to operate their "respiratory burst" biochemistry, with which they kill bacteria. Collagen is essential for rebuilding the damaged tissues, and for creating new blood vessels (angiogenesis), which need collagen fibres on which to construct capillary walls. Collagen synthesis can only take place when hydroxylase enzymes can hydroxylate lysine and proline, to give hydroxy-lysine and hydroxy-proline, both of which are essential building blocks of collagen. Hydroxylase enzymes need a plentiful supply of oxygen for their efficient function. For these reasons, it is widely recognized that wounds must be well oxygenated if they are to heal efficiently, and it is frequently claimed that oxygen supply can be the rate-limiting factor in wound healing. It is believed that a failure to heal is often caused by lack of an adequate oxygen supply. Moreover, a high oxygen tension in a wound inhibits the growth of pathogenic anaerobic bacteria, which are also responsible for malodour production.

For these reasons, certain secondary dressings, such as Tegaderm from 3M Healthcare Ltd or OpSite from Smith & Nephew (Tegaderm and OpSite are Trade Marks), are made from thin polyurethane film coated on one side with an adhesive layer. These are marketed as being relatively permeable to oxygen (and water vapour), because of their particular molecular structure and thin cross section. This is a purely passive effect, and the efficiency of oxygen permeation is inversely related to the thickness of the film.

Hydrogels are not very permeable to oxygen, because they are composed primarily of water, and oxygen is poorly soluble in water. Their permeability to oxygen will also be inversely related to the thickness of the dressing. Hitherto, the only way to increase the level of oxygen in a wound was to administer oxygen to the patient, either by increasing the amount in the blood (e.g. by causing the patient to breathe oxygen-enriched air or placing the patient in a hyperbaric oxygen environment such as that available in a compression chamber), or by applying gaseous oxygen to the wound itself.

As noted above, dressings in accordance with the invention have the ability efficiently to transport oxygen from the ambient atmosphere outside the wound, into the wound bed, especially in cases where the dressing includes a layer of oxidoreductase enzyme, e.g. glucose oxidase, on the outer surface, in contact with the ambient atmosphere. Oxygen from the ambient atmosphere is converted to hydrogen peroxide (catalysed by the oxidoreductase enzyme). Hydrogen peroxide is much more soluble in water than is molecular oxygen, so hydrogen peroxide transport through the dressing (typically through one or more hydrated hydrogels) is generally much more efficient and rapid than that of molecular oxygen. Hydrogen peroxide thus diffuses rapidly through the dressing. When the hydrogen peroxide encounters catalase (which is naturally present in a wound, or which may be included as a component of the dressing), it decomposes to oxygen and water. In this way, oxygen is transported through the dressing in the form of hydrogen peroxide far more efficiently than transport of molecular oxygen. Experiments have shown that the rate of transport of oxygen can be more than doubled in dressings in accordance with the invention as compared with similar dressings without oxidoreductase enzyme. The resulting enhanced oxygen levels potentiate the healing process, as described above.

Dressings in accordance with the invention (or components thereof) are suitably supplied in sterile, sealed, oxygen and water-impervious packages, e.g. laminated aluminum foil pouches.

Dressings in accordance with the invention can be manufactured in a range of different sizes and shapes for treatment of areas of skin e.g. wounds of different sizes and shapes. Appropriate amounts of enzyme, and substrate and iodide if present, for a particular dressing can be readily determined by experiment.

Figure 2:
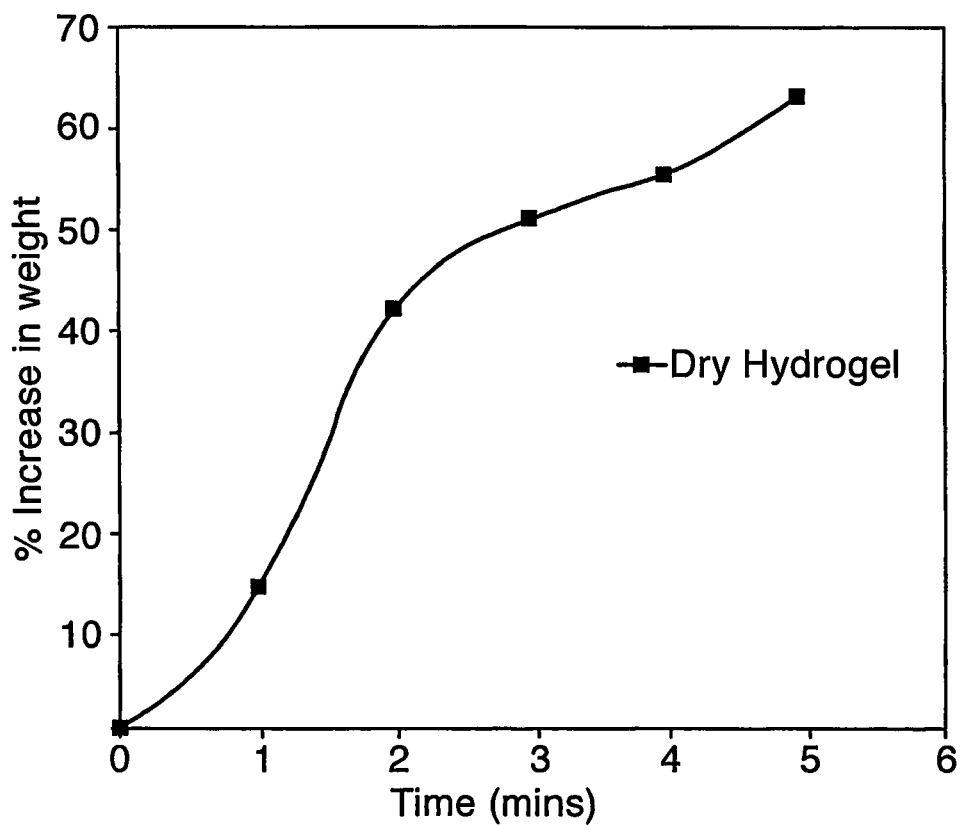
Figure 3:
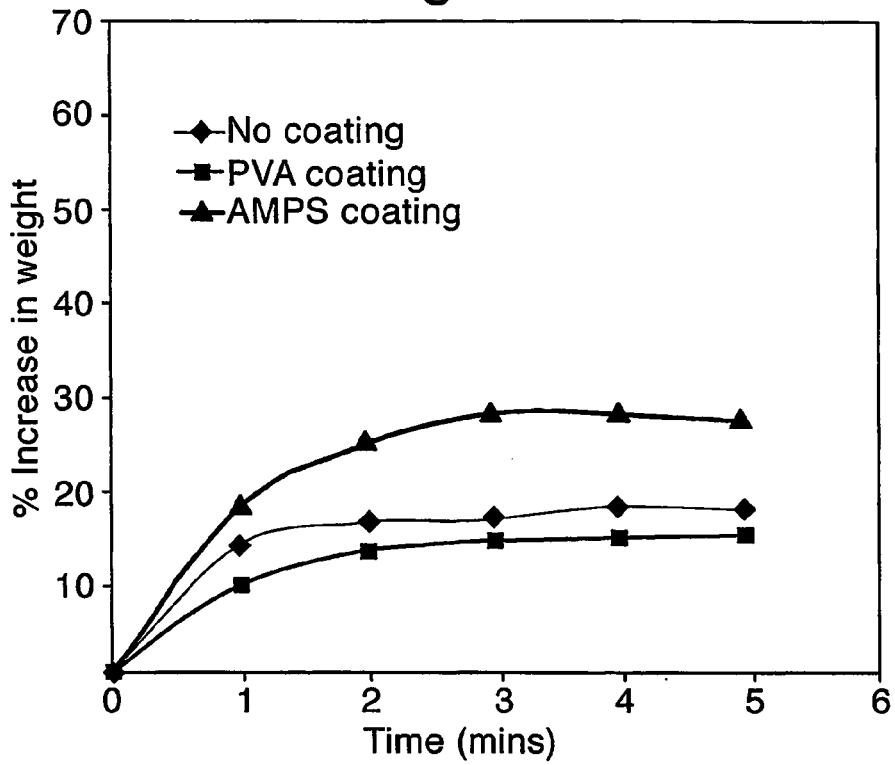
Figure 4:
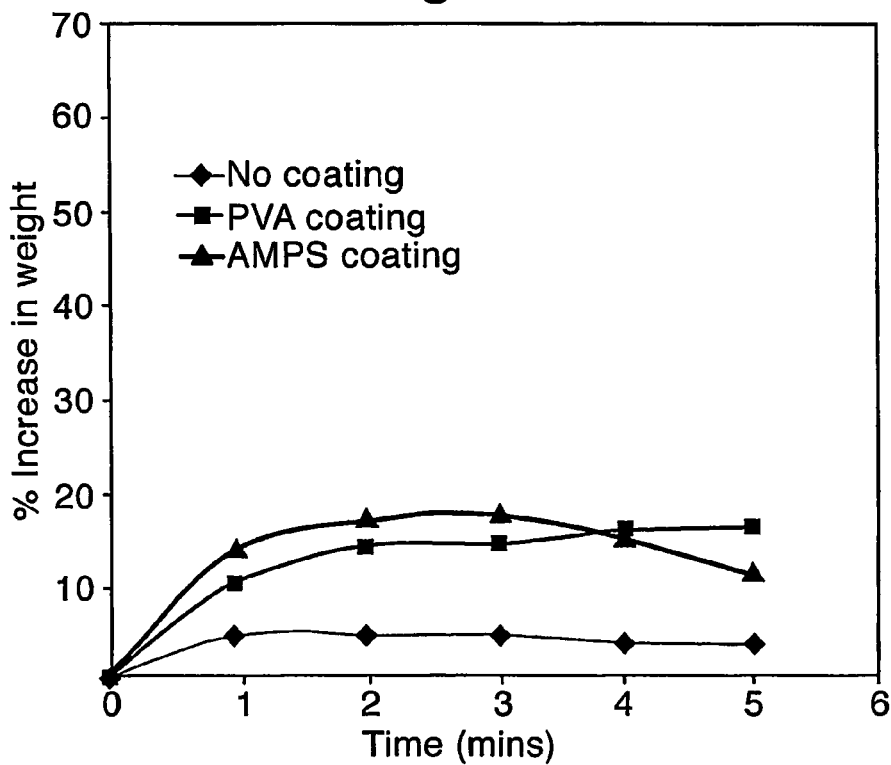

The invention will be further described, by way of illustration, in, the following Examples and with reference to the accompanying drawings, in which:

FIG. 1 is a schematic sectional illustration an embodiment of wound dressing in accordance with the invention; and FIGS. 2 to 4 are graphs of percentage increase in weight versus time (in minutes) illustrating the rate of water uptake of various different layers.

DETAILED DESCRIPTION OF EMBODIMENTS

FIG. 1 illustrates schematically a skin dressing in accordance with the invention.

The illustrated dressing is of layered construction and comprises an outer layer or covering 10 in the form of an oxygen-permeable self-adhesive plaster, suitable for adhering to the skin 12 of a subject, so as to cover a wound 14. Covering 10 encloses an upper layer comprising a first component 16 and a lower layer comprising a second component 18.

The first component 16 comprises a sheet of dried Na poly-AMPS hydrogel incorporating glucose oxidase enzyme, as described below. The second component 18 comprises a sheet of hydrated Na poly-AMPS hydrogel incorporating glucose, as described below.

The dressing is initially supplied as a multi-part system, with the individual components separately packaged in respective sealed, sterile packages. When required for use, the dressing components are removed from the packages and applied to a wound in appropriate manner and order to produce the final dressing as shown.

Details of the gels of components 16 and 18 are as follows.

The hydrogel of the first component was formulated to include the following reagents by weight:
10% sodium AMPS solution, supplied as 50% aqueous solution (2-acrylamido-2-methylpropanesulfonic acid, sodium salt (Lubrizol, code 2405))
0.4% poly ethylene glycol 400 diacrylate (UCB Chemicals) (cross-linking agent, also functioning as solvent for photoinitiator)
0.01% photoinitiator (1-hydroxycyclohexyl phenyl ketone (Aldrich))
0.2% zinc lactate (Sigma) (moisturizer and pH controller)
Glucose oxidase enzyme at 14 U per ml gel
To 100% with deionized (DI)-water.

PEG400 diacrylate was added to the 1-hydroxycyclohexyl phenyl ketone. This was warmed gently for 1-2 minutes to dissolve the photoinitiator. Na AMPS was then added, followed by the glucose oxidase (GOX), zinc lactate and finally the DI-water. The components were then thoroughly mixed.

The mixture was dispensed into a casting tray. A cotton gauze sheet of appropriate size, was then dipped into the monomer solution and removed. The wet gauze was then placed onto a flat surface, and set by irradiation under UV, for 30 seconds under a 1 KW lamp. The hydrogel was then allowed to cool to 30° C. or below before use.

The hydrogel of the second component 18 was formulated to include the following reagents by weight:
20% sodium AMPS (2-acrylamido-2-methylpropanesulfonic acid, sodium salt (Lubrizol, code 2405))
0.2% poly ethylene glycol 400 diacrylate (UCB Chemicals)
0.01% photoinitiator (1-hydroxycyclohexyl phenyl ketone (Aldrich))
20% glucose (Fisher)
0.1% zinc lactate (Sigma)
0.05% potassium iodide (Fisher)
To 100% with DI-water.

PEG400 diacrylate was added to the 1-hydroxycyclohexyl phenyl ketone. This was warmed gently for 1-2 minutes to dissolve the photoinitiator. Na AMPS was then added, followed by the glucose, zinc lactate, potassium iodide and finally the DI-water. The components were then thoroughly mixed.

The mixture was dispensed into a casting tray, to a depth of 2-3 mm. The gel was set by irradiation under UV, for 30 seconds under a 1 KW lamp. The hydrogel was then allowed to cool to 30° C. or below before use.

The dried hydrogel forming the first component 16 is formulated to be optimised to preserve enzyme activity through manufacture, drying, irradiation (to ensure sterility) and storage, and also for extraction of water from the second component 18 on contact therewith, for rehydration of the first component in use of the dressing.

The hydrated hydrogel forming the second component 18 is optimised for skin-contact properties, including the ability to absorb moisture from the skin, eg in the form of wound exudate, while also being able to moisturize a dry surface, eg a dry wound, to which it is applied. Moisturizing effects arise by the hydrogel acting to increase the relative humidity of the skin micro-environment and also by the effect of the lactate moisturizer: water vapour can escape relatively easily from the hydrogel. The hydrogel also functions efficiently as a source of water for donation to the first component 16. The second component hydrogel further provides a large reservoir of glucose substrate at a defined concentration, capable in use of giving a sustained, highly efficient effect at a known and controlled rate.

As noted above, the dressing components 16 and 18 are kept separate before use, e.g. being sealed in separate, sterile, water-impervious packages such as laminated aluminum foil pouches.

In use of the dressing, when the first component 16 contacts the second component 18, water rapidly migrates from the second component to the first component, where it acts to hydrate the glucose oxidase enzyme. Once hydrated, the enzyme acts to catalyse reaction of the glucose substrate in component 18, resulting in generation of hydrogen peroxide with consequent benefits for wound healing.

EXAMPLES

Experiment 1

Experiments were carried out using the dried hydrogel material used for the first component 16 (referred to as layer 1) and the hydrated hydrogel material used for the second component 18 (referred to a layer 2), to demonstrate restoration of the activity of the dried enzyme in layer 1 on rehydration with water stored in layer 2. This involved the use of indicator plates prepared as follows:

1% agar (Sigma) and 1% starch (Aldrich) was dissolved in DI-water. 100 mM potassium iodide (Fisher) was then added, and the molten gel poured into disposable petri dishes to a depth of 2-3 mm. The gels were allowed to cool.

A sheet of layer 1 hydrogel was dried in an oven at 37° C. for 1 hour. 4 cm×4 cm blocks of layer 2 were placed onto indicator plates. To the top of these, either the dried or non-dried layer 1 sheet was added. The rate of colour change was observed as an indicator of how quickly the glucose oxidase is producing hydrogen peroxide. The colour change is due to the hydrogen peroxide oxidising the iodide to iodine, which produces a yellow brown stain within the gel. As the iodine and excess hydrogen peroxide diffuse through the hydrogel, they will interact with the starch and iodide in the indicator plate. The excess hydrogen peroxide will oxidise the iodide to iodine, which in turn combines with the starch to form a blue coloured complex. Table 1 demonstrates the relative intensities of colour generated.

TABLE 1 comparative and qualitative review of colour intensity generated during reaction.

| Time (mins) | Wet Layer 1 Colour Intensity | Dried Layer 1 Colour Intensity |
|---|---|---|
| 0 | — | — |
| 15 | x | xx |
| 30 | xx | xxx |
| 45 | xxx | xxxx |
| 60 | xxxx | xxxxx |
| 75 | xxxxx | xxxxxx |

The results showed that the dried hydrogel sheet surprisingly started to work more quickly than the hydrated hydrogel sheet. Subsequent colour development proceeded at a similar rate, until the entire indicator plates were blue from the starch-iodide complex. This shows that the hydrogel formulation will allow water transfer between the two gels in dried and non-dried states, respectively, and that the layer 2 will surrender water to layer 1.

Experiment 2

Further experiments were carried out using different supports for the dried enzyme layer 1, together with a hydrated hydrogel layer 2 as previously described.

Glucose oxidase was prepared in DI-water, 3% w/v polyvinyl alcohol and AMPS monomer at 14 U/ml. Cotton gauze and Whatman No. 1 blotting paper were saturated with each of the solutions and dried at 37° C. A section of each material of each glucose oxidase (GOX) preparation was then applied to a layer 2 gel, on an indicator plate. Also used where the layer 1 hydrogels described in experiment 1. The samples were observed for colour change (i.e. perceived activity) and wetting. The observations are seen in Table 2 and Table 3 respectively.

These observations show that layer 2 hydrogel will give water to a separate layer that lies in contact therewith. The rate of re-wetting varies depending on the type of material that is used in the upper layer 1. From the observations, using the same monomer material in the upper layer 1 as that in the lower layer 2, water transfer is quicker, thus allowing the movement of enzyme substrate to begin quicker. This is visible by observing how quickly the indicator colour develops and by the wetting of the dried samples.

With a simple upper layer 1 not including any rehydration enhancer materials, enzyme activity is restored at the interface between the layers, but not away from the interface, so not all available enzyme was activated. The enzyme activity restoration at the interface occurred well before there was any visible sign of wetting. Even this limited enzyme activation occurs sufficiently rapidly and is of sufficient extent to be useful in dressings embodying the invention. With a upper layer including a rehydration enhancer material, PVA, AMPS or poly AMPS, enzyme activity is restored more rapidly and within layer 1 as well as at the interface, so it is preferred to use such materials.

Experiment 3

Further experiments were carried out using different materials for the first component 16, i.e. the upper layer of the dressing. In particular, different support materials (absorbent filter paper, cotton gauze and dry poly-AMPS) were used for carrying dried glucose oxidase enzyme, with and without PVA and AMPS as hydration enhancers. The water uptake properties of the different materials on contact with a hydrated Na poly-AMPS hydrogel (second component 18) were examined.

The following experimental first component layers were prepared:
Layer A) Absorbent filter paper
Layer B) Absorbent filter paper coated in PVA, with PVA used at 3% w/v
Layer C) Absorbent filter paper coated in Na AMPS monomer, with Na AMPS monomer used at 20-25% w/v
Layer D) Cotton gauze

TABLE 2 perceived activity after combination of layer 1 and layer 2.

| Time (mins) | Gox in water Gauze | Gox in water Paper | Gox in PVA Gauze | Gox in PVA Paper | Gox in AMPS Gauze | Gox in AMPS Paper | Gox in h/gel Wet | Gox in h/gel Dried |
|---|---|---|---|---|---|---|---|---|
| 1 | — | — | — | — | — | — | — | — |
| 15 | — | — | — | — | x | x | x | x |
| 30 | x | x | x | x | xx | xx | xx | xx |
| 45 | xx | xx | xxx | xxx | xxx | xxx | xxx | xxx |

TABLE 3 observed wetting rate after combination of layer 1 and layer 2.

| Time (mins) | Gox in water Gauze | Gox in water Paper | Gox in PVA Gauze | Gox in PVA Paper | Gox in AMPS Gauze | Gox in AMPS Paper | Gox in h/gel Wet | Gox in h/gel Dried |
|---|---|---|---|---|---|---|---|---|
| 1 | — | — | — | — | — | — | xxx | — |
| 15 | — | — | x | x | xx | xx | xxx | xx |
| 30 | x | x | xx | xx | xxx | xxx | xxx | xxx |
| 45 | xx | xx | xx | xx | xxx | xxx | xxx | xxx |

Layer E) Cotton gauze coated in PVA, with PVA used at 3% w/v

Layer F) Cotton gauze coated in Na AMPS monomer, with Na AMPS monomer used at 20-25% w/v Layer G) Dry poly Na-AMPS The layers were saturated with the coatings then allowed to dry in a temperature controlled oven at 37° C. for 1 hour. The hydrogel layer G was prepared as described above and was also dried under these conditions. AU of the layers contained glucose oxidase at a concentration of 100 μg per gram of gel. The enzyme acts as marker for rehydration: the enzyme becomes activated after migration of sufficient water and this activity can be tested for, providing a qualitative assessment of water uptake. No details are given at such qualitative assessments.

To assess quantitatively the uptake of water, 2.5 cm×2.5 cm squares of the layers A to G were cut. These were then layered onto a base gel (second component 18), which was composed of 20% Na AMPS, 0.2% crosslinker (PEG 400 diacrylate), 0.01% photoinitiator (1-hydroxycyclohexyl phenyl ketone) and 20% glucose, prepared as described above. The weight of the upper layer (A to G) was measured at one minute intervals, to assess quantitatively their water uptake properties. This assessment is independent of enzyme activity.

Results.

The results are shown graphically in FIGS. 2 to 4, with FIG. 2 giving results for a poly Na-AMPS layer (layer G), FIG. 3 giving results for absorbent filter paper layers (layers A, B and C) and FIG. 4 giving results for cotton gauze layers (layers D, E and F).

FIG. 2 shows the ability of the matched base support material, i.e. Na poly-AMPS, to absorb an increased amount of water over the alternative base materials (filter papers, and cotton gauze, FIGS. 3 and 4 respectively). Within the cotton gauze material experiment (FIG. 4) Na AMPS coated base layer will absorb more water than PVA coated base layer, which in turn will absorb more water than just the base gauze only. This shows that the hydration enhancers will actively encourage the absorption of water. The experiment using the absorbent filter paper (FIG. 3) shows the inclusion of Na AMPS monomer also increases the absorption capacity of the base material.

Overall, the key finding is that when using the matched layer construction (i.e. poly Na-AMPS in both top and base layers) water is absorbed more readily and to a higher final volume. This rate of initial uptake can be seen in the graphs of FIGS. 3 and 4, where the sample coated with Na AMPS takes up water quicker than the sample with no coating or the sample coated with PVA. The higher final volume can be seen with reference to the scale used in the graphs. The difference in the rate of water uptake only occurs when the layers are matched.

The invention claimed is:

1. A kit for forming a skin dressing, comprising:
   a first dressing component carrying immobilized oxidoreductase enzyme in dried condition; and
   a second dressing component carrying a source of water;
   wherein a substrate for the immobilized oxidoreductase enzyme is present in at least one of said first and second dressing components;
   wherein the second dressing component is for application to the skin and the first dressing component is for application above the second dressing component distal to said skin to form a skin dressing such that water migrates from the second dressing component towards the first dressing component and acts to hydrate the immobilized oxidoreductase enzyme in the first dressing component at least at the surface of the first dressing component proximate to the second dressing component, with the hydrated immobilized oxidoreductase enzyme catalyzing the conversion of atmospheric oxygen to hydrogen peroxide for transport through the first and second dressing components to the skin for conversion to oxygen, and
   wherein said first and second dressing components are provided separately from one another such that there is no fluid communication therebetween prior to combination on the skin to form a skin dressing.

2. The kit according to claim 1, wherein the oxidoreductase enzyme comprises glucose oxidase.

3. The kit according to claim 1, wherein the substrate is present in the second dressing component.

4. The kit according to claim 1, including a supply of iodide ions.

5. The kit according to claim 1, wherein the first dressing component and second dressing component are in the form of layers.

6. The kit according to claim 1, wherein the first dressing component comprises a support or carrier carrying the immobilized oxidoreductase enzyme.

7. The kit according to claim 6, wherein the support or carrier comprises dried hydrogel material.

8. The kit according to claim 7, wherein the hydrogel comprises hydrophilic polymer material.

9. The kit according to claim 8, wherein the polymer comprises poly(-2-acrylamido-2-methylpropane sulphonic acid) and/or salts thereof.

10. The kit according to claim 8 or 9, wherein the hydrophilic polymer material is present at a concentration of at least 1% by weight based on the total weight of the gel.

11. The kit according to claim 1, wherein the second dressing component comprises a support or carrier carrying water.

12. The kit according to claim 11, wherein the second dressing component comprises a hydrated hydrogel.

13. The kit according to claim 12, wherein the hydrated hydrogel comprises poly(-2-acrylamido-2-methylpropane sulphonic acid) and/or salts thereof.

14. The kit according to claim 13, wherein the second dressing component comprises a hydrated hydrogel comprising 20% by weight of poly(-2-acrylamido-2-methylpropane sulphonic acid) and/or a salt or salts thereof.

15. The kit according to claim 12, 13 or 14, wherein the hydrated hydrogel contains at least 30% by weight water.

16. The kit according to claim 14, wherein the hydrated hydrogel contains about 60% by weight of water.

17. The kit according to claim 1, wherein the first and second dressing components both include gel supports comprising the same polymer.

18. The kit according to claim 1, wherein the first dressing component includes monomers that are identical to monomers from which a polymeric support of the second dressing component is formed.

19. The kit according to claim 1, wherein the first dressing component includes one or more hydration enhancers.

20. The kit according to claim 19, wherein the hydration enhancer is selected from dried sugars, glycerol and sorbitol.

21. The kit according to claim 1, wherein the first dressing component comprises a support of dried hydrogel formed from 10% by weight poly(-2-acrylamido-2-methylpropane sulphonic acid) and/or a salt or salts thereof, carrying enzyme, and the second dressing component comprises a support of hydrated hydrogel comprising 20% by weight of poly(-2-acrylamido-2-methylpropane sulphonic acid) and/or a salt or salts thereof.

22. The kit according to claim 1, wherein the first and/or second dressing component includes one or more moisturizer materials.

23. The kit according to claim 1, including a covering or outer layer for adhering the dressing to the skin of a human or animal subject.

24. The kit according to claim 1, wherein the first and second dressing components are in separate sealed packages.

25. The kit according to claim 10 wherein the concentration of the hydrophilic polymer material is at least 5% by weight based on the total weight of the gel.

26. The kit according to claim 10 wherein the concentration of the hydrophilic polymer material is at least 10% by weight based on the total weight of the gel.

27. The kit according to claim 20 wherein the dried sugar is selected from the group consisting of sucrose and trehalose.

* * * * *